(12) United States Patent
Zchut et al.

(10) Patent No.: US 10,898,525 B2
(45) Date of Patent: Jan. 26, 2021

(54) KRILL OIL PREPARATIONS AND THEIR USES

(71) Applicant: AKER BIOMARINE ANTARCTIC AS, Stamsund (NO)

(72) Inventors: Sigalit Zchut, Haifa (IL); Itay Shafat, Yokneam Ilit (IL); Inbal Eyal, Kiryat Motzkin (IL); Gai Ben-Dror, Gita (IL); Hala Laoz, Kfar Kama (IL); Ofer Bonen, Kibutz Naan (IL)

(73) Assignee: AKER BIOMARINE ANTARCTIC AS, Stamsund (NO)

( * ) Notice: Subject to any disclaimer, the term of this patent is extended or adjusted under 35 U.S.C. 154(b) by 371 days.

(21) Appl. No.: 15/307,764

(22) PCT Filed: Apr. 29, 2015

(86) PCT No.: PCT/IB2015/001599
§ 371 (c)(1),
(2) Date: Oct. 28, 2016

(87) PCT Pub. No.: WO2015/181640
PCT Pub. Date: Dec. 3, 2015

(65) Prior Publication Data
US 2017/0065645 A1    Mar. 9, 2017

Related U.S. Application Data

(60) Provisional application No. 61/986,706, filed on Apr. 30, 2014.

(51) Int. Cl.
*A61K 35/612* (2015.01)
*A23L 33/115* (2016.01)
*A23D 9/013* (2006.01)
*A61K 31/202* (2006.01)
*A61K 31/685* (2006.01)
*A61K 31/683* (2006.01)
*A23D 9/04* (2006.01)

(52) U.S. Cl.
CPC ............ *A61K 35/612* (2013.01); *A23D 9/013* (2013.01); *A23D 9/04* (2013.01); *A23L 33/115* (2016.08); *A61K 31/202* (2013.01); *A61K 31/683* (2013.01); *A61K 31/685* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2011/0223246 A1 | 9/2011 | Opheim | |
| 2011/0268811 A1 | 11/2011 | Minatelli | |
| 2012/0321602 A1* | 12/2012 | Rosedale | A61K 31/662 424/94.1 |
| 2013/0059768 A1 | 3/2013 | Hallaraker | |

FOREIGN PATENT DOCUMENTS

| | | |
|---|---|---|
| EP | 2361513 | 8/2011 |
| WO | 2005/037848 | 12/2012 |
| WO | 2012/172411 | 12/2012 |
| WO | 2014/013335 | 1/2014 |

OTHER PUBLICATIONS

Shyh-Hwa, Liu et al. "Docosahexaenoic acid and phosphatidylserine supplementations improve antioxidant activities . . . " Brain Research, vol. 1451, Feb. 24, 2012, pp. 19-26.
International Search Report, International Patent Application No. PCT/IB2015/001599, dated Nov. 3, 2015.

* cited by examiner

*Primary Examiner* — Terry A McKelvey
*Assistant Examiner* — Catheryne Chen
(74) *Attorney, Agent, or Firm* — Casimir Jones S.C.; J. Mitchell Jones

(57) ABSTRACT

A preparation comprising krill oil and phospholipids. Methods of treatment comprising administering the same.

10 Claims, No Drawings

KRILL OIL PREPARATIONS AND THEIR USES

FIELD OF THE INVENTION

The present invention relates to novel krill oil preparations and their uses.

BACKGROUND OF THE INVENTION

Omega-3 (n-3 or ω-3) polyunsaturated fatty acids (PUFA) are made of at least 16 carbons with multiple unsaturated bonds. These fats are rich in unsaturated chemical bonds, in which the first unsaturated bond is on the third carbon. Among these fatty acids (FAs) are alpha-linolenic acid (ALA, fatty acid with 18 carbons and 3 unsaturated bonds also named 18:3, an omega-3 FA from plant sources), eicosapentaenoic acid (EPA, FA with 20 carbons and 5 unsaturated bonds also named 20:5) and docosahexaenoic acid (DHA, FA with 22 carbons and 6 unsaturated bonds also named 22:6).

The main source of both EPA and DHA are marine sources such as fish. These fatty acids were shown to have positive effects on general human health and on a number of ailments, such as inflammation and inflammatory diseases (Giudetti, A. M., and Cagnazzo, R. (2012) Beneficial effects of n-3 PUFA on chronic airway inflammatory diseases. Prostaglandins & other lipid mediators 99, 57-67), protection from stroke (Larsson, S. C., Orsini, N., and Wolk, A. (2012) Long-chain omega-3 polyunsaturated fatty acids and risk of stroke: a meta-analysis. European journal of epidemiology 27, 895-901), cognitive diseases (Luchtman, D. W., and Song, C. (2013) Cognitive enhancement by omega-3 fatty acids from child-hood to old age: findings from animal and clinical studies. Neuropharmacology 64, 550-565), cardiovascular diseases (CVD) and other heart conditions (FAO/WHO. (2010) Joint FAO/WHO Expert Consultation on the Risks and Benefits of Fish Consumption; Jump, D. B., Depner, C. M., and Tripathy, S. (2012) Omega-3 fatty acid supplementation and cardiovascular disease. Journal of lipid research 53, 2525-2545; Mozaffarian, D., and Rimm, E. B. (2006) Fish intake, contaminants, and human health: evaluating the risks and the benefits. Jama 296, 1885-1899).

Numerous clinical and pre-clinical studies showed that n-3 PUFAs attached to phospholipids (PL-n-3) are better absorbed than n-3 PUFAs attached to triglycerides (TG-n-3). Graf et al. fed radio-isotopes of n-3 bound to phospholipids or triglycerides to rats and tested their absorption to various tissues of the animals. Rats fed with PL-n-3 had significantly higher levels of n-3 PUFA in their brains, hearts and livers (Graf, B. A., Duchateau, G. S., Patterson, A. B., Mitchell, E. S., van Bruggen, P., Koek, J. H., Melville, S., and Verkade, H. J. (2010) Age dependent incorporation of 14C-DHA into rat brain and body tissues after dosing various 14C-DHA-esters. Prostaglandins, leukotrienes, and essential fatty acids 83, 89-96). Wijendran et al. demonstrated that following oral administration to baboons, certain fatty acids reached target tissues such as heart, lung and red blood cell membranes better when bound to phospholipids than to triglycerides (Wijendran, V., Huang, M. C., Diau, G. Y., Boehm, G., Nathanielsz, P. W., and Brenna, J. T. (2002) Efficacy of dietary arachidonic acid provided as triglyceride or phospholipid as substrates for brain arachidonic acid accretion in baboon neonates. Pediatr Res 51, 265-272). The better absorption of PL-n-3 has also been demonstrated in humans. Ramprasath et al (Ramprasath, V. R., Eyal, I., Zchut, S., and Jones, P. J. (2013) Enhanced increase of omega-3 index in healthy individuals with response to 4-week n-3 fatty acid supplementation from krill oil versus fish oil. Lipids in health and disease 12, 178) demonstrated that krill oil with 40% phospholipids has a superior absorption of n-3 PUFAs into the plasma and red blood cells compared with fish oil in which the n-3 PUFAs are attached to triglycerides. It is therefore widely accepted that phospholipids improve the absorption and functionality of n-3 PUFAs.

N-3 PUFAs were shown to have a beneficial effect on ailments related to the metabolic syndrome, including CVD. The metabolic syndrome is a disorder of energy utilization and storage that has become a growing health problem throughout the world. The metabolic syndrome is diagnosed by the presence of at least three out of the following five criteria: abdominal obesity, elevated blood pressure, elevated fasting plasma glucose, high serum triglycerides, and low high-density cholesterol (HDL) levels. The metabolic syndrome is often observed in overweight individuals (Beilby, J. (2004) Definition of Metabolic Syndrome: Report of the National Heart, Lung, and Blood Institute/American Heart Association Conference on Scientific Issues Related to Definition. Circulation 109, 433-438).

The importance of reduction in weight—Obesity has become a major health problem in the Western world. In the United States, the prevalence of obesity increased dramatically and doubled between the 1970s and 2008. This increase is not unique to adults either, as it is noted also in children and adolescents.

Obesity leads to an increased risk for diseases such as type 2 diabetes, heart diseases and certain types of cancer. Since all of these diseases also lead to premature death, overweight and obese individuals also have a reduced life expectancy.

Obesity-associated diseases that were once diagnosed primarily in adults are now also increasingly observed in children and adolescents with excess body fat. Elevation in blood cholesterol and prevalence of type 2 diabetes are now increasing in children and adolescents, with possible adverse effects that may persist throughout the lifespan (USDA. (2010) Dietary Guidelines for Americans 2010).

Other important predictors of heart disease risk are hypertension and elevated heart rate—Data from the USA guideline for nutrition (USDA. (2010) Dietary Guidelines for Americans 2010) reveals that about 34% of U.S. adults suffer from hypertension. There are substantial evidences that reducing blood pressure (BP) decreases the risk of total mortality, cardiovascular mortality and stroke (Cottin, S. C., Sanders, T. A., and Hall, W. L. (2011) The differential effects of EPA and DHA on cardiovascular risk factors. The Proceedings of the Nutrition Society 70, 215-231).

Increased heart rate is positively correlated with hypertension and has only recently emerged as an independent cardiovascular risk factor to be targeted to reduce cardiovascular events, especially in high-risk populations.

Importance of fatty acid distribution in the blood—Plasma profile of fatty acid was shown to influence many of the routine functions of the human body. It might be advantageous to increase the level of certain beneficial fatty acids while decreasing the levels of detrimental fatty acids. Saturated fatty acids, such as palmitic acid, raise total and low-density lipoprotein (LDL) cholesterol, and high consumption of them is included in a definition of unhealthy dietary practices (WHO. (2003) Diet, Nutrition and the Prevention of Chronic Diseases). In a recent meta-analysis, encompassing over 100,000 subjects, total saturated fatty acids were found to increase the risk of CVD (Chowdhury, R., Warnakula, S., Kunutsor, S., Crowe, F., Ward, H. A., Johnson, L., Franco, 0. H., Butterworth, A. S., Forouhi, N.

G., Thompson, S. G., Khaw, K. T., Mozaffarian, D., Danesh, J., and Di Angelantonio, E. (2014) Association of Dietary, Circulating, and Supplement Fatty Acids With Coronary Risk: A Systematic Review and Meta-analysis Annals of internal medicine 160, 398-406). Nonetheless, individual fatty acids were shown to have either a beneficial or detrimental effect. While palmitic acid is an example of a fatty acid with correlations to CVD and other ailments (FAO/WHO. (2010) Joint FAO/WHO Expert Consultation on the Risks and Benefits of Fish Consumption), stearic acid is an example of saturated fatty acid with possible beneficial effects. For example, increasing stearic acid levels in the plasma might be beneficial for reducing mean platelet volume, coagulation factor FVII activity and plasma lipid concentrations, thus decreasing thrombogenic and atherogenic risks (Kelly, F. D., Sinclair, A. J., Mann, N. J., Turner, A. H., Abedin, L., and Li, D. (2001) A stearic acid-rich diet improves thrombogenic and atherogenic risk factor profiles in healthy males. European journal of clinical nutrition 55, 88-96).

Unlike saturated fatty acids, unsaturated fatty acids, mostly long chain polyunsaturated fatty acids, were shown to be beneficial for human consumption from infancy to adulthood. Effects of EPA and DHA are described elsewhere, but alpha linoleic acid (ALA) was also shown to have beneficial effects. Several prospective studies have found an inverse association between the intake of ALA and risk of fatal coronary heart disease (USDA. (2010) Dietary Guidelines for Americans 2010). Others have found that daily intake of flaxseed oil, highly enriched with ALA, improves glycemic control (Hutchins, A. M., Brown, B. D., Cunnane, S. C., Domitrovich, S. G., Adams, E. R., and Bobowiec, C. E. (2013) Daily flaxseed consumption improves glycemic control in obese men and women with pre-diabetes: a randomized study. Nutrition research 33, 367-375).

SUMMARY OF THE INVENTION

The present invention provides a preparation comprising krill oil, wherein the preparation contains an amount of phospholipids and an amount of omega-3 fatty acids such that the ratio (weight/weight (w/w)) of the amount of phospholipids in the preparation to the amount of omega-3 fatty acids in the preparation (phospholipids:omega-3 fatty acids) is 0.5 to 1.6.

The present invention provides a preparation comprising krill oil in which the concentration of phospholipids in the preparation is at least 30% (w/w).

The present invention provides a preparation comprising krill oil, wherein the preparation contains an amount of EPA and an amount of DHA such that the ratio (w/w) of the amount of phospholipids in the preparation to the sum of the amounts of EPA in the preparation and DHA in the preparation (phospholipids:EPA+DHA) is 0.7 to 2.3.

The present invention provides a preparation comprising krill oil in which the concentration of palmitic acid in the preparation is less than 15% (w/w).

The present invention provides a preparation comprising krill oil, wherein the preparation contains an amount of saturated fatty acids and an amount of unsaturated fatty acids such that the ratio (w/w) of the amount of saturated fatty acids in the preparation to the amount of unsaturated fatty acids in the preparation (saturated fatty acids:unsaturated fatty acids) is less than 0.5.

The present invention provides a preparation comprising krill oil in which the concentration of omega-3 fatty acids in the preparation is more than 20% (w/w).

The present invention provides a preparation comprising krill oil in which the concentration of cholesterol in the preparation is less than 1.5% (w/w).

The present invention provides a preparation comprising krill oil wherein the preparation contains an amount of omega-3 fatty acids bound to phospholipids and an amount of omega-3 fatty acids bound to neutral lipids such that the ratio (w/w) of the amount of omega-3 fatty acids bound to phospholipids in the preparation to the amount of omega-3 fatty acids bound to neutral lipids in the preparation (omega-3 fatty acids bound to phospholipids:omega-3 fatty acids bound to neutral lipids) is less than 0.9.

The present invention provides a preparation comprising krill oil wherein the preparation contains an amount of EPA, an amount of DHA, and an amount of Myristic acid such that the ratio (w/w) of the sum of the amount of EPA in the preparation and the amount of DHA in the preparation to the amount of Myristic acid in the preparation (EPA+DHA:Myristic acid) is more than 4.

The present invention provides a preparation comprising krill oil wherein the preparation contains an amount of omega-3 fatty acids and an amount of Myristic acid such that the ratio (w/w) of the amount of omega-3 fatty acids in the preparation to the amount of Myristic acid in the preparation (omega-3 fatty acid:Myristic acid) is more than 5.

The present invention provides a preparation comprising krill oil wherein the preparation contains and amount of EPA, an amount of DHA, and an amount of omega-6 fatty acids such that the ratio (w/w) of the sum of the amount of EPA in the preparation and the amount of DHA in the preparation to the amount of omega-6 fatty acids in the preparation (EPA+DHA:omega-6 fatty acids) is more than 9.

The present invention provides a preparation comprising krill oil wherein the preparation contains an amount of omega-3 fatty acids and an amount of omega-6 fatty acids such that the ratio (w/w) of the amount of omega-3 fatty acids in the preparation to the amount of omega-6 fatty acids in the preparation (omega-3 fatty acids:omega-6 fatty acids) is more than 11.

The present invention provides a nutritional, pharmaceutical, or nutraceutical composition or a functional or medical food comprising any of the preparations described above.

The present invention provides preparations, according to any one of the preparations described above, for use in one or more of: treating of a cardiovascular disease (CVD), treating cognitive disease, treating inflammatory disease, treating obesity, treating abdominal obesity, preventing CVD, preventing cognitive disease, preventing inflammatory disease, preventing obesity, preventing abdominal obesity, reducing high blood pressure, reducing heart rate, reducing blood plasma concentrations of saturated fatty acids, reducing blood plasma concentrations of palmitic acid, increasing blood plasma concentrations of Alpha-Linolenic acid (ALA), and increasing blood plasma concentrations of stearic acid.

The present invention provides preparations, according to any one of the preparations described above, for use in a method for one or more of: treating of a cardiovascular disease (CVD), preventing CVD, treating cognitive disease, treating inflammatory disease, treating obesity, treating abdominal obesity, preventing cognitive disease, preventing inflammatory disease, preventing obesity, preventing abdominal obesity, reducing high blood pressure, reducing heart rate, reducing blood plasma concentrations of saturated fatty acids, reducing blood plasma concentrations of palmitic acid increasing blood plasma concentrations of Alpha-Linolenic acid (ALA) and increasing blood plasma concentrations of stearic acid.

The present invention provides preparations, according to any one of the preparations described above, for treating or preventing one or more condition selected from the group consisting of: cardiovascular disease (CVD), cognitive disease, inflammatory disease, obesity, abdominal obesity, high blood pressure, high heart rate, high blood plasma concentrations of saturated fatty acids, high blood plasma concentrations of palmitic acid, low blood plasma concentrations of Alpha-Linolenic acid (ALA), and low blood plasma concentrations of stearic acid.

The present invention provides preparations, according to any one of the preparations described above, for use in the manufacture of a pharmaceutical composition, a dietary supplement, a medical food, a nutritional or a neutraceutical composition for one or more of: treating of a cardiovascular disease (CVD), treating cognitive disease, treating inflammatory disease, treating obesity, treating abdominal obesity, preventing CVD, preventing cognitive disease, preventing inflammatory disease, preventing obesity, preventing abdominal obesity, reducing high blood pressure, reducing heart rate, reducing blood plasma concentrations of saturated fatty acids, reducing blood plasma concentrations of palmitic acid, increasing blood plasma concentrations of Alpha-Linolenic acid (ALA), and increasing blood plasma concentrations of stearic acid.

The present invention provides a method for one or more of: treating of a cardiovascular disease (CVD), treating cognitive disease, treating inflammatory disease, treating obesity, treating abdominal obesity, preventing CVD, preventing cognitive disease, preventing inflammatory disease, preventing obesity, preventing abdominal obesity, reducing high blood pressure, reducing heart rate, reducing blood plasma concentrations of saturated fatty acids, reducing blood plasma concentrations of palmitic acid, increasing blood plasma concentrations of Alpha-Linolenic acid (ALA), and increasing blood plasma concentrations of stearic acid, comprising administering an effective amount of any of the preparations described above to a subject in need thereof.

DETAILED DESCRIPTION OF THE INVENTION

Krill oil is associated with a positive effect on metabolic risk factors such as reduction in levels of plasma lipids, reduction in cholesterol level, reduction in blood glucose level, reduction in weight, reduction in liver fat and reduction in blood pressure. Krill oil is also associated with reduction in inflammation and in severity of inflammatory diseases. Moreover, krill oil is associated with improved cognitive function, has anti-depressant potential and is linked to improvement in symptoms of premenstrual syndrome.

The present invention provides specific preparations comprising krill oil in which the ratio (w/w) of the amount of phospholipids in the preparations to the amount of omega-3 fatty acids in the preparations is 0.5 to 1.6, which are surprisingly more effective than conventional krill oils in reducing metabolic risk factors and cardiovascular disease risk factors such as high body weight, high blood pressure, high heart rate, high blood palmitic acid level and high saturated fatty acids to unsaturated fatty acids ratio, and in increasing the levels of stearic acid and alpha linolenic acid in the blood.

As used herein the term "treatment" or "treating" refers to obtaining a desired pharmacological and physiological effect on the subject, including prophylactic in terms of "preventing" or partially preventing an undesired condition or symptoms from developing and/or therapeutic in terms of "curing" partial or complete curing of an already existing undesired condition. The term "treating" is used within the context of this application as treatment of subjects who are either healthy or suffer from a disorder, disease, or impaired physiological/medical condition.

As used herein the terms "phospholipids," should be understood to encompass a lipid of the general formula:

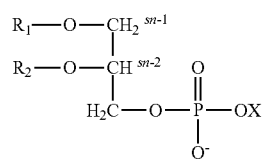

wherein the substituents, R1 (substituent on position sn-1) and R2 (substituent on position sn-2), are independent of each other and are selected from H or an acyl group selected from saturated, mono-unsaturated and polyunsaturated fatty acids, and X represents a moiety selected from serine, choline, ethanolamine, inositol, glycerol and hydrogen.

As used herein, the term "fatty acid' should be understood to encompass a carboxylic acid with a long unbranched aliphatic tail (chain), which is either saturated or unsaturated having one unsaturated bond (mono-unsaturated fatty acids) or two or more unsaturated bonds (poly-unsaturated fatty acids). When referring to a "fatty acid acyl" it should be understood to encompass an —C(=O)—R radical wherein R is a long unbranched aliphatic tail, which is either saturated or unsaturated having one unsaturated bond (mono-unsaturated fatty acids) or two or more unsaturated bonds (poly-unsaturated fatty acids).

Non-limiting examples of saturated fatty acids include: Butyric acid (Butanoic acid, C4:0), Caproic acid (Hexanoic acid, C6:0), Caprylic acid (Octanoic acid, C8:0), Capric acid (Decanoic acid, C10:0), Laurie acid (Dodecanoic acid, C12:0), Myristic acid (Tetradecanoic acid, C14:0), Palmitic acid (Hexadecanoic acid, C16:0), Stearic acid (Octadecanoic acid, C18:0), Arachidic acid (Eicosanoic acid, C20:0), Behenic acid (Docosanoic acid C22:0).

Non-limiting examples of unsaturated fatty acids include: Myristoleic acid (C14:1, ω-5), Palmitoleic acid (C16:1, ω-7), Oleic acid (C18:1, ω-9), Linoleic acid (C18:2, ω-6), Linolenic acid (C18:3) [Alpha-linolenic acid (C18:3, ω-3), Gamma-linolenic acid (C18:3, ω-6)], Eicosenoic acid (C20:1, ω-9), Arachidonic acid (C20:4, ω-6), Eicosapentaenoic acid (C20:5, ω-3), Erucic acid (C22:1, ω-9), Docosapentanoic acid (C22:5, ω-3), Docosahexaenoic acid (C22:6, ω-3), Nervonic acid (C24:1, ω-9).

When reference is made to a " . . . [fatty acid] conjugated to phospholipid . . . ," it should be understood to encompass a phospholipid wherein a fatty acid acyl is conjugated at position sn-1 and/or position sn-2 of the phospholipid backbone (through the glycerol oxygen atom).

The present invention provides preparations comprising at least 30% (w/w) phospholipids, preferably at least 35% (w/w) more preferably at least 40% (w/w) and most preferably at least 42% (w/w) or 45% (w/w).

In one embodiment of the present invention, the ratio (w/w) of the amount of phospholipids in the preparation to the amount of omega-3 fatty acids in the preparation is 0.5 to 1.6, preferably 0.6 to 1.5, more preferably 0.7 to 1.4, even more preferably 0.8 to 1.2 and most preferably 0.8 to 1 or 0.9 to 1.

In another embodiment of the present invention, the ratio (w/w) of the amount of phospholipids in the preparation to the sum of the amount of EPA in the preparation and the amount of DHA in the preparation is 0.7 to 2.3, preferably 0.75 to 1.75, more preferably 0.9 to 1.5 and most preferably 0.9 to 1.3 or 1 to 1.3.

According to another embodiment, the concentration of cl 6 (palmitic acid) in the preparation is less than 15% (w/w), preferably less than 14% (w/w) or 13% (w/w), more preferably less than 10% (w/w) and most preferably less than 9% (w/w) or 8% (w/w).

According to another embodiment, the ratio (w/w) of the amount of saturated fatty acids in the preparation to the amount of unsaturated fatty acids in the preparation is less than 0.5, preferably less than 0.45, more preferably less than 0.4, even more preferably less than 0.35, and most preferably less than 0.3 or 0.2.

According to one embodiment, the preparation of the invention comprises more than 20% omega-3 fatty acids (w/w), preferably more than 30% (w/w), more preferably more than 40% (w/w), even more preferably more than 45% (w/w) and most preferably more than 50% (w/w).

In another embodiment, the concentration of cholesterol in the preparation of the invention is less than 1.5% (w/w), preferably less than 1.2% (w/w), more preferably less than 1.0% (w/w), even more preferably less than 0.7% (w/w) and most preferably less than 0.5% (w/w).

According to another embodiment, the ratio (w/w) of the amount of omega-3 fatty acids bound to phospholipids in the preparation to the amount of omega-3 fatty acids bound to neutral lipids in the preparation is less than 0.9, preferably less than 0.75, more preferably less than 0.6, most preferably less than 0.4.

According to another embodiment, the ratio (w/w) of the sum of the amount of EPA in the preparation and the amount of DHA in the preparation to the amount of Myristic acid (C14) in the preparation is more than 4, preferably more than 10, more preferably more than 12, even more preferably more than 15, most preferably more than 20.

According to yet another embodiment, the ratio (w/w) of the amount of omega-3 fatty acids in the preparation to the amount of Myristic acid (C14) in the preparation is more than 5, preferably more than 10, more preferably more than 15, even more preferably more than 20, most preferably more than 30.

According to yet another embodiment, the ratio (w/w) of the sum of the amount of EPA in the preparation and the amount of DHA in the preparation to the amount of omega-6 fatty acids in the preparation is more than 9, preferably more then 13, more preferably more than 18, even more preferably more than 20, most preferably more than 22.

According to another embodiment the ratio (w/w) of the amount of omega-3 fatty acids in the preparation to the amount of omega-6 fatty acids in the preparation is more than 11, preferably more than 13 or 15, more preferably more than 18 or 20, most preferably more than 25.

The inventive preparation may be manufactured from krill oil as follows. For this process, any krill oil containing phospholipids and omega-3 fatty acids can be used. Optionally, the krill oil may be obtained by organic solvent extraction of krill biomass, whereas the krill biomass may be in the form of meal or in the form of fresh or frozen krill, or in the form of fresh or frozen krill that was processed by cooking and decantation to remove some of the water content.

The krill oil is then processed to increase the phospholipid concentration by fractionation with a solvent. Any solvent, or a mixture of one or more solvents, that will enable separation of a phase containing phospholipids at a higher concentration than in the original krill oil, may be used for this step. Optional solvents are hexane, heptane, acetone, ethanol or water. Krill oil is mixed with a solvent, or a mixture of one or more solvents, and a phospholipids-rich phase is obtained, optionally by gravity phase separation, by centrifugation or by filtration. Optionally, krill phospholipids may be enriched from the krill oil by membrane purification wherein krill oil may be dissolved in organic solvent, preferably hexane or heptane, and the dissolved krill oil may be passed through membranes in which phospholipids will be concentrating in the concentrate side of the membranes while some of the other lipids will be passing selectively to the membrane permeate. The solvents are optionally removed from the phospholipids-rich phase obtained, optionally by evaporation of the solvents, preferably under reduced pressure. Solvents may also be removed after the next process stage in which the phospholipids rich fraction is mixed with other oils.

The phospholipids concentration stage is optionally repeated one or more times in order to achieve the desired phospholipids content: The phospholipids-rich phase is optionally mixed again with one or more solvents as indicated above, and a phase further enriched with phospholipids is obtained, optionally by gravity phase separation, by centrifugation or by filtration. Optionally, the phospholipids-rich phase may be further enriched by membrane purification wherein it may be dissolved in organic solvent, preferably hexane or heptane, and the solution may be passed through membranes in which phospholipids will be concentrating in the concentrate side of the membranes while some of the other lipids will be passing selectively to the membrane permeate. The solvents are optionally removed from the phospholipids-rich phase, optionally by evaporation of the solvents, preferably under reduced pressure. Solvents may also be removed after the next process stage in which the phospholipids rich fraction is mixed with other oils.

The krill oil preparation containing a high concentration of phospholipids is then mixed with one or more oils containing omega 3 fatty acids to prepare the final formulation of the invention. Oils that are used for this step of the formulation process are optionally derived from fish, triglyceride fish oil, ethyl esters fish oil, krill, shrimps, vegetable oils or other known sources. Optionally and preferably, fish oil is used for the mixing with phospholipids. Optionally and preferably, the oils contain more than 30% w/w omega 3 fatty acids, more preferably more than 40% omega 3 fatty acids, even more preferably more than 55% omega 3 fatty acids, and most preferably more than 70% omega 3 fatty acids. The phospholipids enriched krill oil is optionally dissolved in organic solvents (such as hexane, ethanol, acetone or mixture thereof) at the time of the mixing with the oil containing omega 3 fatty acids. The solvents that are used may be the solvents that are left from the phospholipids concentration stage, or other solvents that are added for the formulation stage. In case solvents are used, they are removed after the mixing step. Solvent removal is done preferably by evaporation at reduced pressure. Optionally, the phospholipids enriched krill oil is dried of solvents before the formulation stage, and mixed with omega-3 containing oil "as is," without further dissolution.

The weight ratio between krill oil containing high phospholipids concentration and the omega-3 oil is determined by the desired phospholipids, EPA, DHA, and omega-3 concentrations in the final preparation of the invention.

The preparation of the present invention may be in the form of fluid oil, powder, granules, wax, paste, oil or aqueous emulsion, and any other form that will enable its use. In a further aspect of the present invention, the krill oil preparation is used in conjunction with or is part of a nutritional, pharmaceutical or nutraceutical composition or a functional or medical food.

A nutritional composition as used herein can be any nutritional composition including, but not limited to, human milk fat substitute, infant formula, adult formula, dairy product, milk powder, drinks, ice-cream, biscuit, soy product, bakery, pastry and bread, sauce, soup, prepared food, frozen food, condiment, confectionary, oils and fats, margarine, spread, filling, cereal, instant product, infant food, toddler food, bar, snack, candy and chocolate product.

The pharmaceutical or nutraceutical compositions may be in any of the many dosage delivery forms commonly used in the art. Pharmaceutical compositions suitable for oral administration may be presented as discrete dosage units such as pills, tablets, pellets, dragées, or capsules, or as a powder or granules, or as a solution, suspension or elixir. Suitable routes of administration for the compositions of the subject invention are oral, buccal, sublingual administration, administration via a feeding tube, topical, transdermal, or parenteral (including subcutaneous, intramuscular, intravenous and intradermal) administration. In one embodiment, the compounds are administered orally.

A nutraceutical composition as used herein can be any nutraceutical, which can be any substance that may be considered as a food or part of a food and provides medical or health benefits, including the prevention and treatment of diseases or disorders. Such nutraceutical compositions include, but are not limited to, a food additive, a food supplement, a dietary supplement, genetically engineered foods such as for example vegetables, herbal products, and processed foods such as cereals, soups and beverages and stimulant functional food, medical food and pharmafood. Dietary supplements may be delivered in the form of soft gel capsules, tablets, syrups, and other known dietary supplement delivery systems.

A functional food as used herein can be any functional food, including, but not limited to, dairy product, ice-cream, biscuit, soy product, bakery, pastry, cakes and bread, instant product, sauce, soup, prepared food, frozen food, condiment, confectionary, oils and fats, margarine, spread, filling, cereal, instant product, drinks and shake, infant food, bar, snack, candy and chocolate product.

The exact dose and regimen of administration of the composition will necessarily be dependent upon the therapeutic effect to be achieved and may vary with the particular formula, the route of administration, and the age and condition of the individual subject to whom the composition is to be administered.

The present invention also provides pharmaceutical compositions wherein the preparation is admixed with (pharmaceutically) acceptable auxiliaries, and optionally other therapeutic agents. The auxiliaries must be "acceptable" in the sense of being compatible with the other ingredients of the composition and not deleterious to the recipients thereof. In one embodiment of the present invention, a pharmaceutical composition of the present invention further comprises at least one additional pharmaceutically active agent. The pharmaceutical and nutraceutical compositions may be prepared by any method well known in the art of pharmacy. Such methods include the step of bringing in association the ingredients with any auxiliary agent. The auxiliary agent(s), also named accessory ingredient(s), include those conventional in the art, such as carriers, fillers, binders, diluents, dessicants, disintegrants, lubricants, colorants, flavoring agents, anti-oxidants, and wetting agents.

The pharmaceutical and nutraceutical compositions of the invention may further comprise edible fibers, aroma, taste ingredients, and ingredients that control physical and organoleptic properties.

In another one of its aspects the invention provides a preparation of the invention for use in reducing CVD risk factors, and/or treating or preventing CVD, and/or improving a condition in a subject suffering from CVD and/or improving a condition in a subject suffering from cognitive disease or disorder, and/or treating or preventing cognitive disease or disorder, and/or treating or preventing inflammation or inflammatory disease and/or improving a condition in a subject suffering from inflammation or inflammatory disease or disorder and/or treating or preventing depression and/or improving a condition in a subject suffering from depression and/or treating or preventing premenstrual syndrome and/or improving a condition in a subject suffering from premenstrual syndrome.

In some embodiments of the invention said subject is a toddler. In some embodiments of the invention said subject is a child. In other embodiments, said subject is an adult (including, a male, a female in child bearing age pre or post gestation, a teenager, an elderly senior subject). In other embodiments, said subject is a pregnant or lactating woman.

In one embodiment the invention provides a preparation of the invention for use in one or more of: reducing weight, decreasing blood pressure, reducing heart rate and improving serum lipid profile.

In one embodiment of the invention improvement of lipid profile includes one or more of: increasing at least one omega-3 fatty acids, including EPA, DHA and ALA, as well as stearic acid and reducing unsaturated fatty acids, including palmitic acid.

The term "CVD risk factors" as used herein should be understood to encompass, among others, high blood LDL or total cholesterol or triglyceride levels, low serum HDL cholesterol, elevated serum homocysteine, high blood pressure, inflammation, diabetes and overweight and obesity (NHLBI. (2011) What Are Coronary Heart Disease Risk Factors?).

The term "CVD" as used herein should be understood to encompass any cardiovascular disease or disorder. Non-limiting examples of such a cardiovascular disease or disorder include rheumatic heart disease, heart valve disease, aneurysm, atherosclerosis, peripheral arterial disease, angina, coronary artery disease, coronary heart disease, myocardial infarction, sudden death, cerebrovascular disease, stroke, transient ischemic attacks, cardiomyopathy, pericardial disease, congenital heart disease and heart failure.

The term "cognitive disease or disorder" as used herein should be understood to encompass any cognitive disease or disorder. Non-limiting examples of such a cognitive disease or disorder are Attention Deficit Disorder (ADD), Attention Deficit Hyperactivity Disorder (ADHD), dyslexia, age-associated memory impairment and learning disorders, amnesia, mild cognitive impairment, cognitively impaired non-demented, pre-Alzheimer's disease, Alzheimer's disease, Parkinson's disease, pre-dementia syndrome, dementia, age related cognitive decline, cognitive deterioration, moderate mental impairment, mental deterioration as a result of aging, conditions that influence the intensity of brain waves and/or brain glucose utilization, stress, anxiety, depression, behavior disorders, concentration and attention impairment, mood deterioration, general cognitive and mental well-being, neurodegenerative disorders, hormonal disorders, cognitive disorders caused by concussion or traumatic brain injury or any combinations thereof. In a specific embodiment, the cognitive disorder is memory impairment.

The term "inflammatory disease" as used herein should be understood to encompass any inflammatory disease or disorder. Non-limiting examples of such an inflammatory disease or disorder include rheumatoid arthritis, osteoarthritis, asthma, prostatitis, colitis, Crohn's disease, dermatitis, diverticulitis, glomerulonephritis, interstitial cystitis, irritable bowel syndrome, nephritis, pelvic inflammatory disease, periodontitis, reperfusion injury, sarcoidosis, transplant rejection and vasculitis.

The term "improving a condition" as used herein should be understood to encompass: ameliorating undesired symptoms associated with a disease, disorder, or pathological condition; preventing manifestation of symptoms before they occur; slowing down progression of a disease or disorder; slowing down deterioration of a disease or disorder; slowing down irreversible damage caused in a progressive (or chronic) stage of a disease or disorder; delaying onset of a (progressive) disease or disorder; reducing severity of a disease or disorder; curing a disease or disorder; preventing a disease or disorder from occurring altogether (for example in an individual generally prone to the disease) or a combination of any of the above.

The effective amount of the preparation claimed herein is the dose of this preparation that provides a therapeutic benefit in the treatment or management of the disclosed conditions and diseases. A person skilled in the art would recognize that the effective amount may vary, for example, depending on known factors such as the pharmacodynamic and pharmacokinetic characteristics of the inventive preparation and its mode and route of administration; the age, sex, health and weight of the subject receiving the preparation; the frequency of the treatment and the effect desired; and the kind of the concurrent treatment. A person skilled in the art would also recognize that the effective amount, or dose, of the preparation can be determined based on the disclosures in this patent application and common knowledge in the art.

The amount of the preparation that will be effective in the treatment and/or management of the conditions and diseases disclosed herein can be determined by standard clinical techniques. In vitro or in vivo assays may optionally be employed to help identify optimal dosage ranges.

All of the above mentioned patent documents and scientific research articles are incorporated herein by reference in their entirety.

The following examples further illustrate the present invention, but should not be construed to limit the scope of the invention in any way.

EXAMPLES

Example 1

Lipid Composition of Preparations According to the Invention in Comparison with Conventional Krill Oil

TABLE 1

|  | Preparation of the invention A | Preparation of the invention B | Preparation of the invention C | Preparation of the invention D | Preparation of the invention E | Conventional krill oil |
|---|---|---|---|---|---|---|
| Phospholipids (w/w) | 42% | 42% | 40% | 40% | 40% | 40% |
| Phospholipids: Omega-3 fatty acids | 1.38 | 1.22 | 0.98 | 0.8 | 0.985 | 1.9 |
| Phospholipids: EPA + DHA | 1.69 | 1.52 | 1.13 | 0.91 | 1.14 | 2.18 |
| Palmitic acid (w/w) | 12.7% | 14.2% | 7.5% | 10.3% | 8.42% | 15.1% |
| Saturated fatty acids: unsaturated fatty acids | 0.42 | 0.41 | 0.19 | 0.22 | 0.22 | 0.55 |
| EPA + DHA: C14 | 4.94 | 6.11 | 19.09 | 35.81 | 22.5 | 2.63 |
| Omega-3 fatty acids: C14 | 6.15 | 7.51 | 21.69 | 41.20 | 26.04 | 3.58 |
| EPA + DHA: Omega-6 | 9.90 | 14.41 | 16.70 | 34.62 | 13.4 | 9.22 |
| Omega-3: Omega-6 | 12.32 | 17.72 | 18.97 | 39.83 | 15.5 | 12.53 |

Example 2

Efficacy of the Preparation of the Invention in Comparison with Conventional Krill Oil Experimental design—Twenty healthy human subjects were recruited for a two-phase crossover trial. During the first 4-week treatment phase, the subjects received either 3 gram of conventional krill oil (providing 600 mg of omega-3 PUFA (188 mg DHA and 337 mg EPA) and 1200 mg of krill-phospholipids) or 1.5 grams of preparation E (Table 1) (providing 600 mg of omega-3 PUFA (207 mg DHA and 321 mg EPA) and 600 mg of krill-phospholipids) per day.

Following a washout phase of 8 weeks, the subject received one of the aforesaid two treatments regimens for another 4 weeks. All subjects completed the 2 phases of the study with 95% compliance in terms of consumption of the treatment capsules.

Anthropometric measures following consumption of krill oil vs. the preparation of the invention—Anthropometric measures were performed at baseline and endpoint of each intervention phase (Table 2). A statistically significant decrease in body weight was observed following 4 weeks consumption of the preparation of the invention compared to the conventional krill oil. In addition, BMI and waist circumference measurements also demonstrated a reduction following administration of the preparation of the invention. Furthermore, blood pressure (systolic and diastolic) and heart rate were reduced as well following administration of the preparation of the invention in comparison with conventional krill oil administration.

TABLE 2

(anthropometric measures)

| Parameter | Treatment | Baseline | Endpoint | % Change | Change (Difference) |
|---|---|---|---|---|---|
| Body Weight (Kg) | Krill oil | 67.53 ± 2.75 | 67.96 ± 2.63 | 0.88 ± 0.78 | 0.43 ± 0.37 |
| | Preparation E | 67.99 ± 2.77 | 67.74 ± 2.73 | −0.29 ± 0.35* | −0.25 ± 0.22* |
| BMI (kg/m$^2$) | Krill oil | 23.62 ± 0.68 | 23.75 ± 0.63 | 0.76 ± 0.81 | 0.13 ± 0.15 |
| | Preparation E | 23.79 ± 0.71 | 23.69 ± 0.71 | −0.37 ± 0.35 | −0.10 ± 0.08 |
| Waist (cm) | Krill oil | 77.95 ± 1.98 | 78.20 ± 1.93 | 0.38 ± 0.42 | 0.25 ± 0.27 |
| | Preparation E | 78.25 ± 2.03 | 77.81 ± 2.05 | −0.56 ± 0.44 | −0.43 ± 0.37 |
| Hip (cm) | Krill oil | 92.04 ± 1.19 | 92.45 ± 1.14 | 0.47 ± 0.38 | 0.41 ± 0.34 |
| | Preparation E | 92.69 ± 1.22 | 92.92 ± 1.20 | 0.27 ± 0.30 | 0.23 ± 0.28 |
| Waist/Hip ratio | Krill oil | 0.85 ± 0.02 | 0.84 ± 0.02 | −0.13 ± 0.51 | 0.00 ± 0.00 |
| | Preparation E | 0.84 ± 0.02 | 0.84 ± 0.02 | −0.91 ± 0.36 | −0.01 ± 0.00 |
| Systolic BP (mmHg) | Krill oil | 106.80 ± 2.63 | 108.14 ± 2.00 | 1.67 ± 1.32 | 1.35 ± 1.39 |
| | Preparation E | 106.35 ± 2.45 | 103.97 ± 2.73* | −2.17 ± 1.49 | −2.38 ± 1.56 |
| Diastolic BP (mmHg) | Krill oil | 71.45 ± 1.69 | 72.53 ± 1.32 | 1.89 ± 1.27 | 1.09 ± 0.88 |
| | Preparation E | 71.17 ± 1.96 | 70.5 ± 1.86 | −0.57 ± 1.75 | −0.67 ± 1.34 |
| Heart rate (Beats/min) | Krill oil | 71.35 ± 2.43 | 70.25 ± 1.72 | −0.20 ± 2.83 | −1.10 ± 2.07 |
| | Preparation E | 73.25 ± 2.23 | 69.1 ± 1.74 | −4.91 ± 2.16 | −4.15 ± 1.70 |

*indicates statistically significant different between the krill oil and the preparation of the invention (preparation E)
Values are expressed as Mean ± SEM.
n = 20.

The effect of preparation E on plasma fatty acid composition of test subjects compared with the effect of conventional krill oil on the same—Plasma total lipids were extracted using the Folch method (Folch, J., Lees, M., and Sloane Stanley, G. H. (1957) A simple method for the isolation and purification of total lipides from animal tissues. J Biol Chem 226, 497-509) which involved chloroform-methanol (2:1, v/v) containing 0.01% BHT (Sigma-Aldrich, Oakville, ON, Canada) and heptadecanoic acid as an internal standard (Sigma-Aldrich, Oakville, ON, Canada). Extracted fatty acids were methylated with methanolic HCl. Fatty acid methyl esters were separated on a Supelcowax 10 column (30 m×0.25 mm with 0.25 mm film thickness; Supelco, Bellefonte, Pa., USA) using gas chromatograph equipped with a flame ionization detector (Bruker 430). The oven was programmed from 70 to 240 degrees C. with the following temperature steps (70 degrees C. for 2 min, rise of 30 degrees C./min, 180 degrees C. for 1 min, rise of 10 degrees/min, 200 degrees C. for 2 min, rise of 2 degrees C./min, 220 degrees C. for 4 min, rise of 20 degrees/min, 240 degrees for 6 min). Samples were analyzed with a 20:1 split ratio; helium was used as the carrier gas with a column flow rate of 1.0 ml/min. Temperatures of the injector and detector were set at 270 and 290 degrees C., respectively. Individual fatty acids were identified by comparison with known standards (NuChek Prep, Inc., Elysian, Minn., USA). The concentrations of individual fatty acids were calculated according to the peak area relative to the total area and expressed as the percentage of total fatty acids (i.e., g/100 g).

TABLE 3

(daily dose of administrated fatty acids in the tested preparations)

| | Daily dose of fatty acid | |
|---|---|---|
| Fatty acid concentration (g/100 g) | Krill Oil | Preparation of the invention (E) |
| C16 (Palmitic) | 0.45 | 0.13 |
| C18 (Stearic) | 0.03 | 0.01 |
| C18:3n3 (alpha-Linolenic) | 0.05 | 0.01 |
| C20:2n6 (Eicosadienoic) | 0.00 | 0.00 |
| C20:5n3 (Eicosapentaenoic) | 0.35 | 0.36 |
| C22 (Behenic) | 0.00 | 0.00 |
| C22:5n3 (Docosapentaenoic) | 0.01 | 0.03 |
| C22:6n3 (Docosahexaenoic) | 0.21 | 0.25 |
| Total omega3 fatty acids | 0.75 | 0.70 |
| Total omega6 fatty acids | 0.06 | 0.03 |
| Total Saturated fatty acids | 0.74 | 0.17 |
| Total PUFA | 0.83 | 0.73 |

TABLE 4

(change of fatty acid concentration in plasma of test subjects following administration of conventional krill oil in comparison to the administration of the preparation of the invention)

| | Change in % FA in plasma/total FA | |
|---|---|---|
| Fatty acid concentration (g/100 g) | Krill oil supplementation | Supplementation of the preparation of the invention (E) |
| C16 (Palmitic) | −0.37 | −2.09* |
| C18 (Stearic) | −0.04 | 0.12* |
| C18:3n3 (alpha-Linolenic) | −0.05 | 0.10* |
| C20:2n6 (Eicosadienoic) | 0.00 | 0.03* |
| C20:5n3 (Eicosapentaenoic) | 1.26 | 1.22 |
| C22 (Behenic) | −0.04 | −0.12* |
| C22:5n3 (Docosapentaenoic) | 0.15 | 0.22* |
| C22:6n3 (Docosahexaenoic) | 1.02 | 1.29* |
| Total omega3 fatty acids | 2.38 | 2.72 |
| Total omega6 fatty acids | −0.68 | −2.48* |
| Total Saturated fatty acids | −0.56 | −3.16* |
| Total PUFA | 1.70 | 0.25* |

*statistically significant difference between groups (p < 0.05).
FA = Fatty acids.

As can be seen in Table 4, stearic acid levels in the test subjects' plasma decreased following krill oil intake. Surprisingly, consumption of the preparation of the invention resulted in a significant increase in stearic acid plasma levels although the administered control krill oil contains higher stearic acid levels than the preparation according to the invention (Table 3). Similarly, plasma levels of ALA were reduced after krill oil consumption, but increased following consumption of the preparation of the invention. The change in ALA plasma levels between the groups was statistically significant although the preparation of the invention contains only a fifth of the amount of ALA found in the conventional krill oil (Table 3).

Furthermore, the consumption of krill oil, providing 0.74 g of saturated fatty acids per day (Table 3), resulted in a decrease in the plasma level of saturated fatty acids and especially of palmitic acid (Table 4). Consumption of the preparation of the invention, providing a daily dose of 0.17 g saturated fatty acids (Table 3), resulted in a decrease in the plasma levels of saturated fatty acids, specifically palmitic acid, that were at least 5-fold lower than the levels after conventional krill oil consumption (Table 4).

What is claimed is:

1. An encapsulated preparation comprising Krill oil, wherein the krill oil comprises omega-3, myristic and palmitic fatty acids, wherein the encapsulated preparation contains an amount of phospholipids and an amount of omega-3 fatty acids such that the ratio (w/w) of the amount of phospholipids to the amount of omega-3 fatty acids is 0.5 to 1.6, wherein the concentration of palmitic acid in the preparation is less than 15% (w/w), wherein the preparation contains an amount of saturated fatty acids and an amount of unsaturated fatty acids such that the ratio (w/w) of the amount of saturated fatty acids to the amount of unsaturated fatty acids is less than 0.5, and wherein the preparation contains an amount of EPA, an amount of DHA, and an amount of myristic acid such that the ratio (w/w) of the sum of the amount of EPA and the amount of DHA to the amount of myristic acid is more than 4.

2. The preparation of claim 1, wherein the concentration of phospholipids in the preparation is at least 30% (w/w).

3. The preparation of claim 1, wherein the preparation contains an amount of EPA and an amount of DHA such that the ratio (w/w) of the amount of phospholipids to the sum of the amount of EPA and the amount of DHA is 0.7 to 2.3.

4. The preparation of claim 1, wherein the concentration of omega-3 fatty acids in the preparation is more than 20% (w/w).

5. The preparation of claim 1, wherein the concentration of cholesterol in the preparation is less than 1.5% (w/w).

6. The preparation of claim 1, wherein the preparation contains an amount of omega-3 fatty acids bound to phospholipids and an amount of omega-3 fatty acids bound to neutral lipids such that the ratio (w/w) of the amount of omega-3 fatty acids bound to phospholipids to the amount of omega-3 fatty acids bound to neutral lipids is less than 0.9.

7. The preparation of claim 1, wherein the preparation contains an amount of omega-3 fatty acids and an amount of myristic acid such that the ratio (w/w) of the amount of omega-3 fatty acids to the amount of myristic acid is more than 5.

8. The preparation of claim 1, wherein the preparation contains and amount of EPA, an amount of DHA, and an amount of omega-6 fatty acids such that the ratio (w/w) of the sum of the amount of EPA and the amount DHA to the amount of omega-6 fatty acids is more than 9.

9. The preparation of claim 1, wherein the preparation contains an amount of omega-3 fatty acids and an amount of omega-6 fatty acids such that the ratio (w/w) of the amount of omega-3 fatty acids to the amount of omega-6 fatty acids is more than 11.

10. A method of treating or preventing one or more condition selected from the group consisting of: cardiovascular disease (CVD), cognitive disease, inflammatory disease, obesity, abdominal obesity, high blood pressure, high heart rate, high blood plasma concentrations of saturated fatty acids, high blood plasma concentrations of palmitic acid, low blood plasma concentrations of Alpha-Linolenic acid (ALA), and low blood plasma concentrations of stearic acid, comprising administering an effective amount of the preparation of claim 1 to a subject in need thereof.

* * * * *